United States Patent [19]

Grudem

[11] Patent Number: 4,708,130

[45] Date of Patent: Nov. 24, 1987

[54] LUMBAR DYNAMIC SPLINT

[76] Inventor: Charles M. Grudem, 6088 Foxtail Dr., White Bear Lake, Minn. 55110

[21] Appl. No.: 897,792

[22] Filed: Aug. 18, 1986

Related U.S. Application Data

[63] Continuation-in-part of Ser. No. 702,384, Feb. 15, 1985.

[51] Int. Cl.$^4$ ............................ A61F 5/02; A61F 5/04
[52] U.S. Cl. .................................. 128/78; 128/89 R; 128/90
[58] Field of Search ............... 128/78, 85, 74 R, 74 B, 128/89 R, 90

[56] References Cited

U.S. PATENT DOCUMENTS

| | | | |
|---|---|---|---|
| 2,434,883 | 1/1948 | Hittenberger | 128/95 |
| 3,620,211 | 11/1971 | Goodell | 128/89 R |
| 3,871,367 | 3/1975 | Miller | 128/78 |
| 4,202,327 | 5/1980 | Glancy | 128/90 X |
| 4,245,627 | 1/1981 | Mignard | 128/78 |
| 4,285,336 | 8/1981 | Oebser et al. | 128/78 |

Primary Examiner—Robert A. Hafer
Assistant Examiner—Kathleen J. D'Arrigo
Attorney, Agent, or Firm—Thomas B. Tate

[57] ABSTRACT

The invention is a lumbar dynamic splint made of low temperature thermoplastic material and designed to provide an exact contour fit to the patient's body. The device comprises a vertical back piece, a chest piece, a right pelvis arm, a left pelvic arm, two vertical front struts, two chest strap anchors, and a chest strap.

1 Claim, 3 Drawing Figures

LUMBAR DYNAMIC SPLINT

This application is a continuation in part of application Ser. No. 702,384, filed 2/15/85, now abandoned.

SUMMARY AND BACKGROUND OF THE INVENTION

The invention is a lumbo-sacral orthotic device, also known as a lumbar dynamic splint, designed to support or immobilize the spine during recovery from injury and/or surgery. It may also have applications in prevention of lumbar spine injury.

Most lumbar immobilization devices currently available are one of two types - elastic band supportive garments or plastic or cast material body jacket devices that are applied to the patient.

The object of the present invention, which is made of light-weight pliable materials that support patients, fit easily and comfortably, and are easily applied, is to provide an effective lumbar support device which is more comfortable for the patient to wear than most devices currently available, more effective than others, and less expensive than some.

Figure 1:
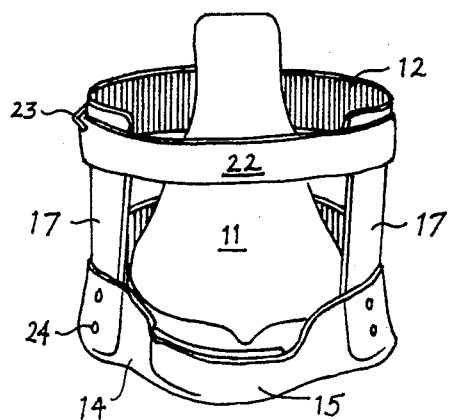
FIG. 1 is a front view.
Figure 2:
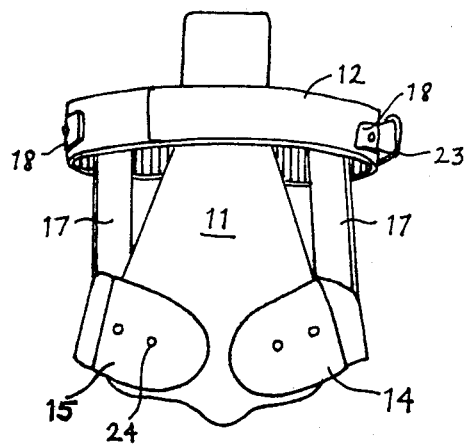
FIG. 2 is a back view.
Figure 3:
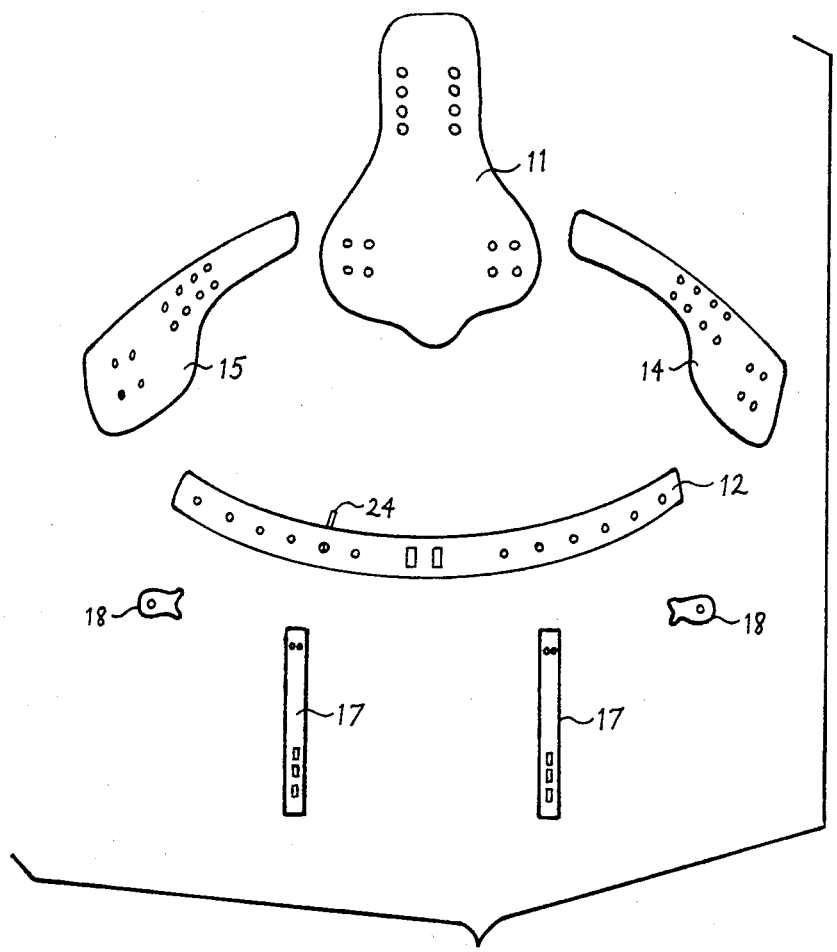

DESCRIPTION OF THE PREFERRED EMBODIMENT OF THE INVENTION:

The lumbar dynamic splint comprises a vertical back piece 11, a chest piece 12, a right pelvic arm 14, a left pelvic arm 15, two vertical front struts 17, and two chest strap anchors 18. All of these pieces (except the chest strap anchors, which are made of standard plastic) are made of low temperature thermoplastic material, of which polycaprolactone, commercially available under the brand name Aquaplast, is a well-known example.

All of the plastic pieces (except the chest strap anchors 18) are lined with closed cell foam padding. The pelvic arms 14 and 15 are provided with Velcro fasteners. A chest strap 22 is attached to the chest strap anchors 18 by means of D-rings 23. The chest strap anchors 18 and D-rings 23 may be combined into one piece. A plurality of screw posts 24 are fitted through openings in the aforementioned plastic pieces to hold said pieces together.

Because there are various hole or slot positions in the plastic pieces, the lumbar dynamic splint can be adjusted to fit adults of various sizes. Exact contour fitting to an individual patient's body is a unique feature of this invention which can be accomplished by warming the plastic as hereinafter described.

The following instructions for cutting, packaging, fitting, and using the lumbar dynamic splint illustrate the best mode for making and using the invention, but it should be understood that other processes may be used in making and fitting the invention and that the scope of the invention shall include all modifications incorporating the structure claimed herein.

LUMBAR DYNAMIC SPLINT (L.D.S.) CUTTING AND PACKAGING PROCEDURES

The following cutting procedures utilize the AQUAPLAST brand 3/16" thick thermoplastic material for the Lumbar Dynamic Splint and a ⅛" to 3/16" thick closed cell foam which is water and heat resistant and has an adhesive backing. Also used are ¼" diameter aluminum screw posts; plastic 2" 'D' rings; and 1½" to 2" wide Velcro material. A template has been made for cutting paterns of this device, in anticipation of possible die cutting of both foam and plastic materials. The standard sheet of 3/16" thick AQUAPLAST is 25" wide and 49¾" long.

Each L.D.S. is comprised of 6 pieces of low temperature plastic of unique shapes, with the following connotations:
  A. Vertical back piece.
  B. Chest Piece.
  C. Right "pelvic" arm.
  D. Left "pelvic" arm.
  E. Vertical front struts (2).
(and)
  Chest strap anchors (2) standard plastic.

The foam cutting pattern is almost identical with the exception that there are two shorter pieces of foam for the one chest piece. The foam is also ¼" wider than the corresponding plastic. The chest strap anchors are not padded. Thereby, each L.D.S. has 7 pieces of foam for it.

In addition, there are 16 aluminum screw posts and 1 chest strap per L.D.S. The chest strap is approximately 24" to 33" long. Two nylon "D" rings, 2" in size, are also part of each L.D.S., and are attached to the strap anchors, as described below. All holes on the plastic material are intended to be ¼" in diameter to accommodate the ¼" diameter screw posts.

Five different templates have been prepared. One template is the 25" long chest piece and it has hole locations marked and pre cut for the center and at both ends. The outermost holes are designed for the chest strap anchors. The other holes are designed for adjustable positions of the vertical struts and for attachment to the back piece. The second template is the vertical back piece. The holes marked on the lower part are for the attachment of the pelvic arms and the upper holes are for the chest piece. The third template outlines the lateral strut pattern. The upper horizontally placed holes are for the attachment to the chest piece and the lower vertical holes are for the attachment to the pelvic arms. The fourth template is for the lateral "pelvic" arms, and has holes for attaching to the backpiece and vertical struts. A fifth template is used for cutting the foam for the pelvic arms.

The procedure for cutting and packaging the materials is as follows:

CUTTING:

1. The template patterns for all plastic pieces are laid out on the sheet of AQUAPLAST. These are then outlined on the plastic sheet. These may then be cut with a band saw or die.
2. The holes are marked and drilled or punched out.
3. The foam patterns are cut out in a similar fashion, and mounted. Again, the foam is to be approximately ¼" wider and longer than the plastic, to wrap over the edges of the corresponding plastic piece.
4. The chest foam pieces, however, may be cut from a piece of foam that is 10" by 18" (width of the roll) and you can get six of the 3" wide and 10" long strips from this. This is enough for 3 braces.
5. The holes are cut in all of the foam materials after mounting on their respective plastic pieces, with the exception of the vertical struts, which have no holes, in the padded area 6. The 4" to 5" long pieces of the vertical strut foam padding are then cut. They may or may not be mounted to the center of the plastic struts at this time.
7. The larger end of each of the pelvic arm foam pieces is cut to shape by using the special template provided. Then, using the other markings on this template, the rest of the patterns for each pelvic foam arm are marked and then cut.
8. It is noted that the left pelvic arm foam is also shorter at the narrow end, compared to the right "arm". The flat edge of the foam material is to be mounted up along the flat edge of the plastic piece. The soft non-adhesive surfaces are to be facing toward the patient.

ASSEMBLING:

9. All foam pieces are secured in place by removing the adhesive backing and pressing the foam firmly into position. The foam pads should overlap the edges of the plastic piece by approximately $\frac{1}{8}$" or so. The larger end, where the holes are, is not padded. Similarly, the central $4\frac{1}{2}$" of the inside of the posterior chest piece is not padded. This allows plastic to plastic contact.
10. Next, the Velcro for the "pelvic arms" is attached to the narrow parts of each pelvic "arm" with a heating process or an adhesive of some sort. Attention must be paid to insuring that the Velcro "hook" surface is on the outer surface of the inner arm and the "loop" Velcro is on the inner surface of the outermost arm. This assures proper contact between the Velcro components and avoids skin contact with the "hooks". The Velcro is attached as a $1\frac{1}{2}$" to 2" strip starting from the narrow end of the piece and going towards the larger end. This strip is about 10" long. This loop type Velcro is on the same side of the brace as the shorter piece of foam.
11. On the pelvic arm that has the longer piece of foam, the strip of Velcro hook type material is then placed horizontally from the narrow end towards the larger, and paralleling the flat surface at the top of the plastic piece. It should be noted that this hook Velcro is on the side opposite the foam.
12. The chest strap loop anchors (two) are each prepared from a $2\frac{1}{2}$" long piece of AQUAPLAST that is 2" wide. About 1" of the length will be single thickness and the remaining $1\frac{1}{2}$" of the length is heated to a translucent or soft condition, and then doubled back around the flat part of a 2" "D ring" loop. This "D ring" is held in place while the doubled back plastic is pressed together firmly and allowed to harden. A $\frac{1}{4}$" hole is then drilled (when plastic is cool and hard) in the center of the single thickness part, for a screw post to fasten the anchor to the chest piece.
13. The chest strap is made of a soft material with some small degree of elasticity. The strapping will accept and hold hook type Velcro, at least 4" of which is sewn onto each end of the cloth/foam strap material. The hook Velcro is sewn onto the ends so as to make proper contact with the strap after passing through and wrapping around a "D ring".

PACKAGING:

14. The aluminum screw posts are inserted into the various holes on the device, for use by the customer. The chest strap is attached to the plastic anchors. (These will be removed by the customer for shaping). The screw posts are placed in the L.D.S. in such a fashion as to indicate their probable final location for the average large adult, except that where two posts will connect one plastic piece to another, there would be only one which actually connects the two separate pieces. The second such post would go through only one of the pieces. This allows the piece to be rotated into a packaging position which requires a minimum amount of space. The chest piece is not attached to the back piece for packaging but it is attached as described here to the vertical front struts, chest strap anchors and chest strap. The back piece is also attached accordingly, by one screw post (on each side) to the two pelvic arms which are then swung up to nearly parallel the long portion of the back piece for packaging.
15. When the above procedures are completed, there will be two sets of pieces to be put in the L.D.S. box. One set will include the padded vertical back piece and two padded pelvic arms, attached to each other with a single screw post on each side. The rest of the screw posts will be in place on one part of this set. The other set of parts is comprised of the padded chest piece and those parts that attach to it. The padding for each vertical strut is attached (now) to the plastic strut by a rubber band, instead of using the adhesive backing. That padding will be attached by the adhesive later in the fitting process.
16. The informational booklets entitled, "This is Your Lumbar Dynamic Splint" and "The L.D.S. Fitters Guide" are then placed inside the box, which is then closed, labelled, and prepared for storage and/or shipment.

LUMBAR DYNAMIC SPLINT - FITTING PROCEDURES

The Lumbar Dynamic Splint, or L.D.S., is an innovative new low back support device, which features versatility, optimal custom fit and comfort, and ease of application, at a reasonable cost. It is explicitly intended that the fitter be thoroughly familiar with the information booklet, "This Is Your Lumbar Dynamic Splint" and other materials enclosed with the product and/or provided separately. It is also assumed that the fitting technician is experienced in the use of orthopedic splinting devices and is knowledgeable in such principles, including techniques, complications, precautions, etc., some of which is explained in the referred to booklet.

The physical therapist, orthotist, or fitting technician will need to have access to a Hydrocollator and/or other standard heat source such as a heat gun, screw driver and possibly some of the other supplies listed below. A tube of water based lubricating jelly such as "K-Y" will also be of assistance in preventing sticking (that is referred to in the information booklet) as the device is formed. Additional supplies that may be of assistance in the fitting process include:

1. One or two "transfer belts" or a wide "weight lifter belt" and an oversized leather belt, at least 1" wide.
2. A standard wheelless walker of adjustable height.

3. A small tube of gel type "super glue".
4. Heavy duty bandage scissors (or equivalent).
5. For extremely small or large patients, a ¼" leather punch or drill might be of assistance in placing customized holes.
6. 6" wide ace bandage (or equivalent).

It is important to realize that the heating characteristics of the plastic which has foam or Velcro on it are different than those of the plastic without such attachments/covering. Those areas to which other materials are attached will generally heat slower in the Hydrocollator and cool/harden slower than the bare plastic. This low temperature thermoplastic has "memory" capability and returning it closer to its original flat shape is possible by simply heating it and allowing it to cool on a flat surface. Additionally, the plastic is quite sticky when it is hot and can easily be stretched and reformed. If overheated to the point where the plastic is translucent or transparent, this stretchability can be exaggerated and interfere with adequate fitting and/or increased time required for the fitting process. The material can easily be cut with a bandage scissors, especially if warm. In the cooled and hardened state, it may be scored and broken by folding back and forth repeatedly over the scored line. Alternatively, a saw might be used to cut the harder material. Sharp edges should be trimmed back or heated and pressed out.

RECOMMENDED PROCEDURE

The Lumbar Dynamic Splint comes to you pre-packaged and partially pre-assembled. You will want to note the positions of the screw posts and splint parts for further reference, as you continue the fitting process. There should be enclosed in your L.D.S. package/kit: One vertical upright back piece, one horizontal chest piece, two horizontal "pelvic arms", (one right and one left), two vertical front struts and two chest strap anchors. Additionally, there should be enclosed a cloth strap with velcro, this fitters instruction manual and the informational booklet, entitled "This Is Your Lumbar Dynamic Splint". The following procedure is generally recommended, but it is recognized that variations from this procedure can be done safely, if such are within the expertise and interest of the fitter (and patient):

1. The L.D.S. should be examined for completeness of parts and any obvious flaws in material or workmanship. If such is discovered, the manufacturer should be contacted, as indicated in the informational booklet.
2. A rough estimate of the patient's size will assist in determining whether the "pelvic arm" portions will attach with four screw posts on the outer set of holes or four to eight screw posts, using the inner set of holes on the back piece (sacral portion).
3. It should be verified that the patient has, indeed, read the booklet. This might be accomplished during the fitting process, since there will be some time required for the material to harden while being held in place.
4. The patient should be in his or her undergarments, as will routinely be used during the wearing of this splint. A cloth patient gown may also be used over the underclothes, as an option.
5. This splint should be fitted in the upright standing position and it may be of assistance to provide a walker for the patient to use for weight bearing with the arms, during the fitting process. Alternatively, two tables placed close enough to the thighs to allow such weight bearing or additional support by the arms, is also worth considering. It might also be useful to have the edge of a table or a wall in front of the patient, so as to allow them to resist forward pressure that may be exerted manually by the fitter.
6. The chest strap and chest piece should be approximated around the patient's chest to make sure that it is of adequate size for the patient.
7. It is suggested that "K-Y" jelly be handy, so as to allow the fitter to make manual pressure on a warm brace, without sticking to it.
8. We recommend that you begin with the upright vertical back piece and warm the lower half of this part first. Again, the plastic should be warm and moldable, but not transparent. The vertical back piece should be placed up against the patient's sacrum area, with the lowest projection/point being opposed directly to the sacral coccygeal junction as a reliable and palpable land mark, by which the splint can be reapplied repeatedly in the fitting process. The warmed splint may then be pressed against the patient's sacrum and sacroiliac joint areas and low lumbar region, manually, and held in that position until it begins to take some firmness. Alternatively and/or possibly following this step, a firm lubricated pad of a non-adherent material might be placed against the lumbar area and then held firmly in place with a belt or strap. This strap should be wide enough to avoid unintentional indentation of the low back piece. The fitter may want to experiment somewhat with different types of pads and belts. Again, careful attention should be paid to the adhesive properties of the warmed plastic.
9. If this portion of the splint is held in place extrinsically (with a belt or strap), then the fitter may be able to start the next stage of the fitting process.
10. One of the two "pelvic arms" is then heated by immersing in the Hydrocollator. We suggest that the wider end which does not have foam on it is not immersed fully or at least for the full amount of time required for the other areas. Because there is no foam, it will warm more quickly than the remainder of the piece. As the main portions of this piece are softened to a moldable state, the piece is then removed from its hot water immersion and placed around the patient in the appropriate location. The flat edge is up and the foam padding is toward the patient. You should note that the foam should be about ¼" away from the outer margin of the sacral portion of the upright piece. It may be necessary to cut back the foam somewhat for the smaller patient, where the inner set of holes are used on the upright portion, as opposed to the outer set for most patients. This piece is then pressed into shape around the pelvic crest and attention is paid to contouring this under the outer edge of the rim of the pelvis. This contour should be as closely approximated to the patient as possible, to assure good stability of the finished splint. Having wrapped this piece around the patient, it is then held in place manually, or with a combination of broad straps and belt. Meticulous attention should again be paid to avoiding pressure points of a focal nature.

Once the pelvic arm is shaped, it can be temporarily secured in place by the use of the screw posts, lining up the holes on the posterior portion. Attention should be paid to avoiding an excessive buckling of the brace at the junction of the two pieces. Some contouring is permissible at the margin of the upright back piece.

11. The same process is repeated for the other pelvic arm. Any excessive length of this piece may be trimmed back, using a bandage scissors on the warm plastic/Velcro combination. At least 6" of overlapping of Velcro to Velcro contact should be present in the finished splint. Sharp points should also be avoided.

12. The plastic chest piece is then molded to the patient's contours, as was done with the other portions. One-half of the piece is done at a time and it is also secured in place with the screw posts for the initial trial use of the L.D.S. The horizontal chest piece should be at a level just beneath the tips of the scapula and should wrap around the chest, into the axilla at least. Very small patients may require shortening of the device, with additional holes being punched or drilled to accommodate the proper placement of the vertical struts and chest strap anchors. The chest piece is then held in position during the hardening process.

13. The chest strap anchors are then affixed to the most anterior holes of each side of the posterior chest piece and assurances should be made that the arms do not rub up against this uncomfortably.

Once the chest piece is hardened, the chest strap may be applied and its position verified as at the level of the xiphoid process (junction of the inferior rib margins at the midline).

14. The last step in this initial fitting process is one of attaching the vertical struts. Usually, the hole alignment will be fairly good but the struts themselves can be warmed and distorted somewhat, to assure excellent alignment in keeping with the position of the other portions of the splint. If warmed, the cooling process should be allowed (or encouraged), before the Lumbar Dynamic Splint is used for its structural support/restraint purposes.

Following the initial fitting and complete hardening of the splint, all screw posts should be secured tightly and fit should be verified with the patient as being comfortable. The fitter should look for pressure points or sharp edges that might irritate the patient's skin and make any modifications necessary to accomplish such a comfortable fit. After wearing the L.D.S. for a few days or weeks, another fitting verification should take place and if desired, the plastic to plastic contact points can be reinforced by either of the solidifying processes referred to in the information booklet. Additional screw posts may be placed or, preferably, those present can be further secured with "super glue" and/or the plastic contact can be strengthened through the abrading and heating process, with pressure holding the two plastic parts together after heating. Alternatively, a gel type "super glue" may be used between the plastic to plastic contacts.

Any problems encountered during the fitting process should be brought to our attention and any suggestions for expediting it would also be appreciated. Although this description of the fitting process is quite detailed, experience will expedite the time involved and it will be quite simple. With experience, the low temperature thermoplastic and other materials will certainly be appreciated as to their placement and adjustment.

V. POSSIBLE USES OF THE LUMBAR DYNAMIC SPLINT

The reader of this booklet is referred to earlier sections on legal considerations, medical precautions and warnings and should understand these and other sections before prescribing, applying or using the device.

The professional back care provider may wish to consider the following possible uses of the L.D.S. when deciding if, when and how to use it:

1. Acute Lumbar and Lumbosacral Sprain Management

Musculoligamentous injuries elsewhere in the body (other than the spine) have clearly been well treated by early application of splinting devices under appropropriate circumstances. The affordable custom fit Lumbar Dynamic Splint allows this principle to be applied to strain and sprain type injuries of the spine, as well.

When used for this condition, it must be borne in mind that more serious injuries (such as disc or ligament disruption) may not be immediately obvious and may only become apparent by failure of the patient to respond to treatment of what is presumed to be a "sprain" or "strain".

The practitioner should pay careful attention to neurologic signs, symptoms and muscle retraining and rehabilitation before, during and after use of the L.D.S. for this condition. Short term continuous use (for days) may be useful under these circumstances. Use for several weeks should generally include significant time out of the splint and gradual withdrawal of the splint along with appropriate exercise.

2. Intermittent Symptomatic Splinting

In the management of chronic low back pain from injury, the possibility of a significant sprain, with residual weakness, should be entertained. Additionally, disc injury can present an almost identical syndrome but have a slowly progressive degenerative course. In such cases where surgery is not considered appropriate or timely, the versatile L.D.S. allows for partial symptom relief through its external stabilization properties. Patients with typical "mechanical low back pain" can also benefit from Lmited use in support of their low backs, during times of maximum symptomatology. Preliminary utilization in such patients, including those with mild to moderate discogenic instability syndrome offers an alternative which may adequately improve the patient's discomfort, to the point where surgery can be delayed or, occasionally, avoided for an indefinite time period.

When the L.D.S. is utilized for these purposes of temporary partial splinting, it is recommended that careful explanation is given to the patient, regarding the amount of time intended and that such be limited to a few hours per day or a couple of days in a row. The potential (theoretical) for muscle atrophy should be weighed carefully against the benefits of reducing the intensity and/or severity of the "flare-up". Obviously, the patient should be closely supervised during this time to assure that neurologic signs or others do not develop or worsen and/or other conditions occur that would warrant changes in therapy.

A patient who has a chronic and relatively stable set of symptoms that are not of adequate magnitude or type to warrent surgical intervention may actually be able to utilize this device for symptomatic flare-ups, with the precautions listed above and elsewhere in this booklet.

However this Lumbar Dynamic Splint is utilized for intermittent symptomatic splinting, it should be part of a total spine care program, involving periodic professional surveillance and re-evaluation.

3. Instability Diagnosis Verification

Theoretically and practically, adequate immobilization of the lumbar spine is sometimes used as one of several tests in determining the presence of "segmental instability", or "discogenic instability". In the pre-surgical setting, the favorable response to brief periods of more continuous splinting (along the lines of days or weeks) followed by removal of the splinting process and reoccurrence of the instability symptoms, may serve as an aid to verification of the diagnosis of lumbar "instability".

Preliminary experience with this device suggests that such a favorable response, followed by worsening upon removal of the splint, is often correlated with positive discography, positive magnetic resonance scan evidence of disc degeneration, and/or other clinical and radiographic findings of "instability". Adequate controlled studies do not exist to date, supporting this theoretical usage, but such are in progress at the time of this booklet's printing. Some practitioners have indicated that favorable response through external stabilization is probably a predictor of a favorable response to internal stabilization (fusion) if concomitant pathology is also correctd at the time of surgery.

4. Pre and Post Fusion Stabilization

When a lumbar instability patient (with or without herniation) is being prepared for surgical stabilization, this device might possibly assist in the reduction of pre-operative symptoms and thereby improve pain control and/or narcotic needs. Preliminary experience with the L.D.S. in operative patients, also suggests that such might be the case post-operatively.

Obviously, in the post-fusion patient, careful attention needs to be paid to the adequacy of the splinting position and time of utilization on a daily and long-term basis. If prolonged splinting is needed, the device should normally be removed gradually on a decreasing use basis over a significant period of time, during which careful attention is paid to the adequacy and success of the surgical stabilization procedure and rehabilitation/retraining of the spine's muscular support. This may also include exercises and other treatment modalities, including careful and judicious restriction of work and non-work activities, ambulation and movement of the spine.

5. Exercise Versus Splint

The principle of "dynamic splinting" as used elsewhere in orthopedics and rehabilitation, allows guidance of a bocy part and resistance to movement in a controlled fashion during therapeutic exercise as a matter of recondtioning. Although experiece in this technique is lacking, some early users of the Lumbar Dynamic Splint have suggested that this may be a significant advantage over other low back bracing products. Certain parts of the L.D.S. might be removed or loosened for this purpose, but a physician trained in some rehabilitation technique should be consulted before considering this application in any particular patient.

6. "Platform" for Neuromuscular Stimulation

At the time of this booklet printing, only preliminary use of the L.D.S. for this application has begun. Theoretically, the electrodes for a transcutaneous electrical nerve stimualtor (T.E.N.S.) could be permanently affixed with hypoallergenic ("paper type") tape, once a satisfactory placement has been found by traditional techniques. Other electronic stimulation (electromagnetic or neuro-functional electrical stimulation) has not yet been attempted, using this device.

7. Other Applications

Utilization other than for those described above should be considered only after extensive experience is gained with it and with appropriate informed consent as to the relatively experimental use of the product for such purposes. The information contained in the booklet should be reviewed by all parties involved in such innovative uses. Initial experience with a cloth type restraint device (applied in a different fashion than the L.D.S.) and some experience with other low back supports used in an industrial setting, suggest that workers wearing an external garment may actually reduce their risk of injury. It is suspected that this is on the basis of restraining the patient from inappropriate body mechanics and serving as a reminder of the need for careful attention to the low back when doing physically laborious work. The Lumbar Dynamic Splint could also conceivably be used in this fashion, presuming the user and the prescriber find the potential benefits to outweigh the potential risks.

I claim:

1. A lumbar dynamic splint made of low temperature thermoplastic materials which are moldable to produce an exact contour fit to the patient's body, said splint comprising:

a vertical back piece, the lower portion of said back piece being wider than the upper portion, said back piece being of sufficient length to extend from the lower thoracic region to the sacrum and sacroiliac regions of most adult humans, said length being approximately 12 inches to 26 inches, inclusive:

a horizontal chest piece attached to the upper portion of said back piece, said chest piece having two ends, each of which is adapted to extend part way around the chest of the patient to approximately the level of the front of the patient's armpit;

two chest strap anchors attached to said chest piece, one at each of said ends of said chest piece, each of said anchors having an attached D-ring;

a chest strap attached to said D-rings of said chest strap anchors;

two lateral pelvic arms attached to the lower portion of said back piece, said pelvic arms curving around and attaching to each other in front by overlapping Velcro means;

two vertical lateral struts attached to said chest piece and to said pelvic arms;

closed cell foam padding adhesively affixed to the inner surfaces of said back piece, said chest piece, said pelvic arms, and said struts;

said attachments of said chest piece to said back piece, of said chest strap anchors to said chest piece, of said pelvic arms to said back piece, and of said struts to said chest piece and to said pelvic arms, being made by means of screw posts inserted through any of a plurality of openings formed in said pieces, said multiple openings allowing adjustment of said splint to fit almost any size adult.

* * * * *